United States Patent [19]
Sachse

[11] Patent Number: 6,057,923
[45] Date of Patent: May 2, 2000

[54] OPTICAL PATH SWITCHING BASED DIFFERENTIAL ABSORPTION RADIOMETRY FOR SUBSTANCE DETECTION

[75] Inventor: Glen W. Sachse, Yorktown, Va.

[73] Assignee: The United States of America as represented by the Administrator of the National Aeronautics and Space Administration, Washington, D.C.

[21] Appl. No.: 09/290,954

[22] Filed: Apr. 13, 1999

Related U.S. Application Data

[60] Provisional application No. 60/082,355, Apr. 20, 1998.

[51] Int. Cl.$^7$ ..................................................... G01N 21/21
[52] U.S. Cl. ........................................... 356/364; 359/246
[58] Field of Search ..................................... 356/364–370, 356/432–444; 359/246, 245, 238, 239, 281, 885, 888, 891; 250/338.5, 339.13, 347, 349, 330, 338.1, 339.11

[56] References Cited

U.S. PATENT DOCUMENTS

| | | |
|---|---|---|
| 4,489,239 | 12/1984 | Grant et al. . |
| 4,507,558 | 3/1985 | Bonne . |
| 4,567,366 | 1/1986 | Shinohara . |
| 4,759,628 | 7/1988 | Tatsuno et al. . |
| 4,818,705 | 4/1989 | Schneider et al. . |
| 4,841,149 | 6/1989 | Martin et al. . |
| 4,845,356 | 7/1989 | Baker . |
| 4,924,095 | 5/1990 | Swanson, Jr. et al. . |
| 4,963,742 | 10/1990 | Abernathy . |
| 4,999,498 | 3/1991 | Hunt et al. . |
| 5,076,699 | 12/1991 | Ryan et al. . |
| 5,117,676 | 6/1992 | Chang . |
| 5,128,797 | 7/1992 | Sachse et al. . |
| 5,210,702 | 5/1993 | Bishop et al. . |
| 5,252,828 | 10/1993 | Kert et al. . |
| 5,306,913 | 4/1994 | Noack et al. . |
| 5,319,199 | 6/1994 | Stedman et al. . |
| 5,343,043 | 8/1994 | Johnson et al. . |
| 5,343,736 | 9/1994 | Cady et al. . |
| 5,371,367 | 12/1994 | DiDomenico et al. . |
| 5,401,967 | 3/1995 | Stedman et al. . |

OTHER PUBLICATIONS

D. E. Burch and J.D. Penbrook, "Instrument to monitor $CH_4$, CO, and $CO_2$ in auto exhaust," Environmental Protection Agency, Washington, DC, EPA Rep. 650/2–73–030, Oct. 1973.

Sachse, G. W., Patent Application Serial No.: 09/019,473, filed Feb. 5, 1998, "Multi–Gas Sensor".

*Primary Examiner*—Frank G. Font
*Assistant Examiner*—Tu T. Nguyen
*Attorney, Agent, or Firm*—Kurt G. Hammerle

[57] ABSTRACT

A system and method are provided for detecting one or more substances. An optical path switch divides sample path radiation into a time series of alternating first polarized components and second polarized components. The first polarized components are transmitted along a first optical path and the second polarized components along a second optical path. A first gasless optical filter train filters the first polarized components to isolate at least a first wavelength band thereby generating first filtered radiation. A second gasless optical filter train filters the second polarized components to isolate at least a second wavelength band thereby generating second filtered radiation. The first wavelength band and second wavelength band are unique. Further, spectral absorption of a substance of interest is different at the first wavelength band as compared to the second wavelength band. A beam combiner combines the first and second filtered radiation to form a combined beam of radiation. A detector is disposed to monitor magnitude of at least a portion of the combined beam alternately at the first wavelength band and the second wavelength band as an indication of the concentration of the substance in the sample path.

10 Claims, 9 Drawing Sheets

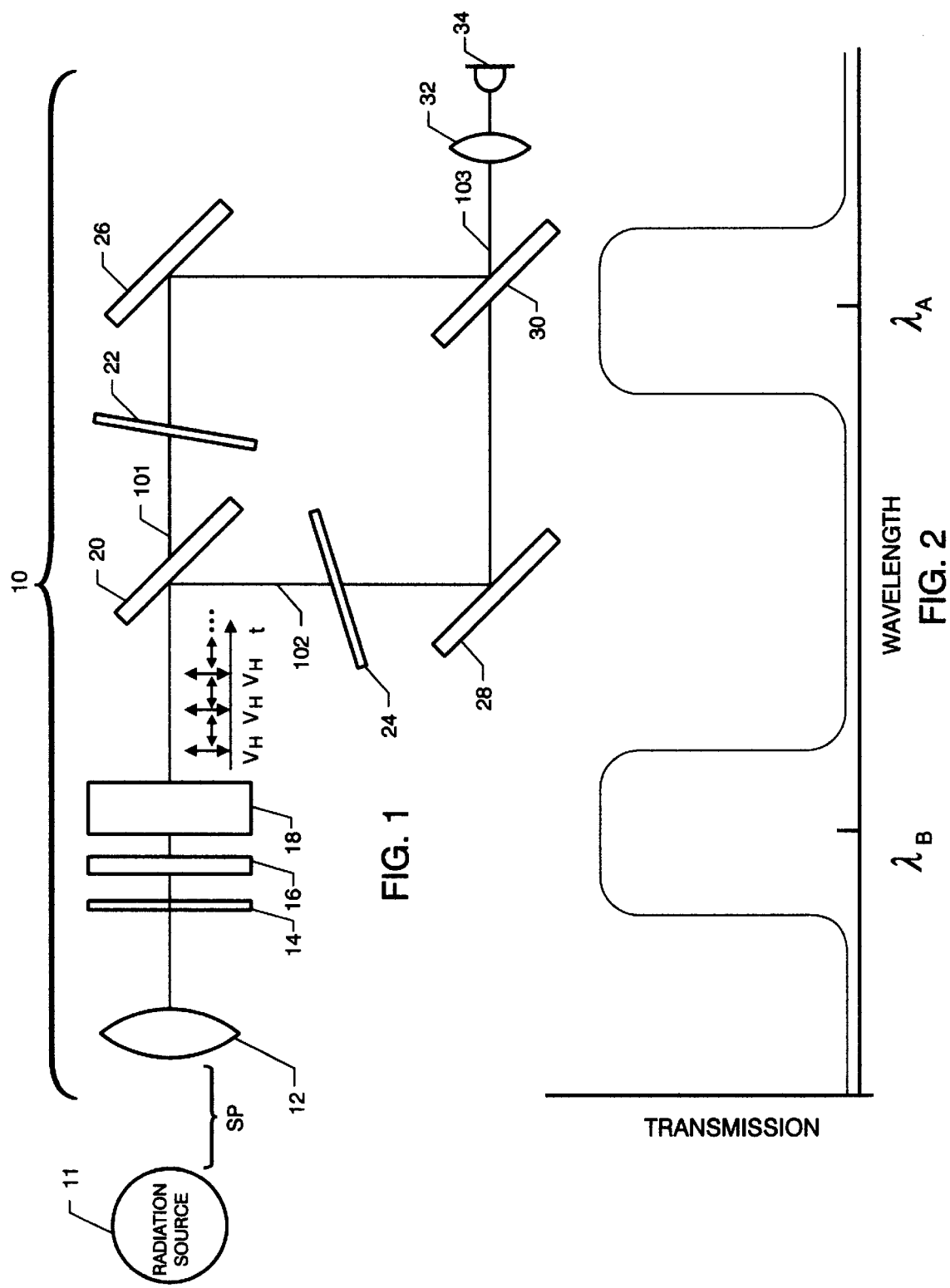

OPTICAL PATH SWITCHING BASED DIFFERENTIAL ABSORPTION RADIOMETRY FOR SUBSTANCE DETECTION

CLAIM OF BENEFIT OF PROVISIONAL APPLICATION

Pursuant to 35 U.S.C. Section 119, the benefit of priority from provisional application 60/082,355, with a filing date of Apr. 20, 1998, is claimed for this non-provisional application.

ORIGIN OF THE INVENTION

The invention described herein was made by an employee of the United States Government and may be manufactured and used by or for the Government for governmental purposes without the payment of any royalties thereon or therefor.

BACKGROUND OF THE INVENTION

1. Field of the Invention

This invention relates to substance detection using optical systems. More specifically, the invention is a method and system for detecting the presence and/or concentration of a substance in a sample path using polarization-modulated optical path switching and the principles of differential absorption radiometry.

2. Description of the Related Art

Gas filter correlation radiometers (GFCRs) infer the concentration of a gas species along some sample path either external or internal to the GFCR. In many GFCRs, gas sensing is accomplished by viewing alternately through two optical cells the emission/absorption of the gas molecules along the sample path. These two optical cells are called the correlation and vacuum cells. The correlation cell contains a high optical depth of gas species i that strongly absorbs radiation at specific molecular transition wavelengths of the particular gas while passing all other wavelengths. In effect, the correlation cell defines a plurality of spectral notches (i.e., strong attenuation) coincident with the band structure of gas species i. The vacuum cell generally encloses a vacuum or a gas or gas mixture exhibiting negligible or no optical depth, e.g., nitrogen, an inert gas, or even clean dry air. An optical filter (e.g., interference filter) placed in front of the instrument or in front of the detector limits the spectral information to a region coinciding with an absorption band of the gas of interest. The difference in signal strength between these two views of the emitting/absorbing gas species i can be related to the concentration of this gas along the sample path.

A known GFCR for measuring concentration of a single gas is disclosed in U.S. Pat. No. 5,128,797, issued to Sachse et al. and assigned to the National Aeronautics and Space Administration (NASA), the specification of which is hereby incorporated by reference. The GFCR includes a non-mechanical optical path switch that comprises a polarizer, polarization modulator and a polarization beamsplitter. The polarizer polarizes light (that has crossed a sample path after originating from a light source) into a single, e.g., vertically polarized, component which is then rapidly modulated into alternate vertically and horizontally polarized components by a polarization modulator. The polarization modulator may be used in conjunction with an optical waveplate. The polarization modulated beam is then incident on a polarization beamsplitter which transmits light of one component, e.g., horizontally polarized, and reflects light of a perpendicular component, e.g., vertically polarized. The transmitted horizontally polarized beam is reflected by a mirror, passes through a gas correlation cell and on to a beam combiner. The reflected vertically polarized beam passes through a vacuum cell, is reflected by a mirror and is passed on to the beam combiner. The beam combiner recombines the horizontal and vertical components into a single beam which passes through an optical interference filter that limits the spectral content of the incoming radiation to an absorption band of the gas species of interest. The single beam is then incident on a conventional detector. However, this system is limited in that it can only measure a single gas concentration.

A GFCR for measuring multiple gases based on the same optical path switching technique is disclosed in U.S. patent application, Ser. No. 09/019,473, filed Feb. 5, 1998, by Sachse et al. and assigned to the National Aeronautics and Space Administration (NASA). In this system, each optical path contains one or more cells with each cell having spectral features of one or more gases of interest. The two optical paths are then intersected to form a combined polarization modulated beam which contains the two orthogonal components in alternate order. The combined polarization modulated beam is partitioned into one or more smaller spectral regions of interest where one or more gases of interest has an absorption band. The difference in intensity between the two orthogonal polarization components in each partitioned spectral region of interest is then determined as an indication of the spectral emission/absorption of the light beam along the sample path. The spectral emission/absorption is indicative of the concentration of the one or more gases of interest in the sample path.

Both of the afore-described systems require the use of gas correlation cells. However, there are instances where gas correlation cells are not practical. For example, some gases are too dangerous and/or require a gas correlation cell construction that is too expensive for a particular application. Further, some gases such as ozone are too reactive to contain in a gas cell. Still further, it may also be desirable to detect/measure a broad category of gases, e.g., hydrocarbons. However, to accomplish this with a GFCR system, many gases would have to be contained within one cell or the beam would have to be passed through multiple gas cells. This complicates construction and adds to overall system expense. Still further, gas correlation cells are not useful for measuring spectral absorption characteristics of solids or liquids because these substances have broad absorption features.

SUMMARY OF THE INVENTION

Accordingly, it is an object of the present invention to detect/measure any type of substances (i.e., gas, liquid or solid) in a non-mechanical optical fashion without the need for gas correlation cells.

Another object of the present invention is to provide a method and system for detecting/measuring broad categories of gases using optical path switching techniques.

Other objects and advantages of the present invention will become more obvious hereinafter in the specification and drawings.

In accordance with the present invention, a system and method are provided for detecting one or more substances. An optical path switch receives radiation passing along a measurement or sample path of interest. The switch divides the radiation into a time series of alternating first polarized components and second polarized components that are orthogonal to the first polarized components. The first polarized components are transmitted along a first optical path and the second polarized components along a second optical path. A first gasless optical filter train disposed in the first optical path filters the first polarized components to isolate at least a first wavelength band thereby generating first filtered radiation. A second gasless optical filter train disposed in the second optical path filters the second polarized components to isolate at least a second wavelength band thereby generating second filtered radiation. The first wavelength band and second wavelength band are unique. Further, spectral absorption of a substance of interest is different at the first wavelength band as compared to the second wavelength band. A beam combiner disposed to receive the first and second filtered radiation combines same to form a combined beam of radiation. A detector is disposed to monitor magnitude of at least a portion of the combined beam alternately at the first wavelength band and the second wavelength band as an indication of the concentration of the substance in the sample path.

BRIEF DESCRIPTION OF THE DRAWINGS

FIG. 1 is a schematic representation of one embodiment of a substance detection system according to the present invention;

FIG. 2 is a graphical illustration of the filter characteristics of the bandpass filters used in the FIG. 1 embodiment;

DETAILED DESCRIPTION OF THE INVENTION

Figure 3:
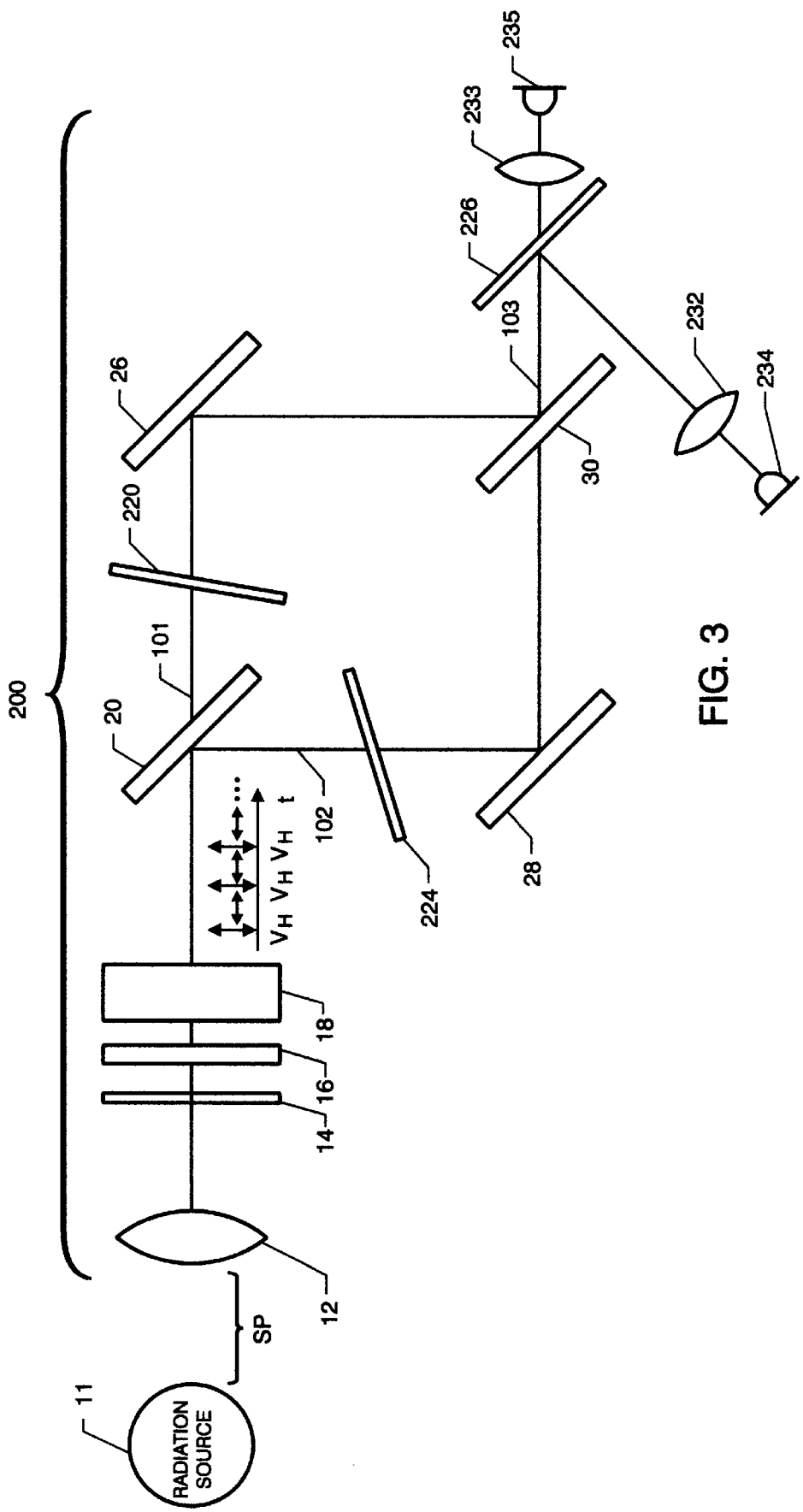
FIG. 3 is a schematic representation of another embodiment of the present invention in which two substances can be detected/measured simultaneously.

Referring now to the drawings, and more particularly to FIG. 1, one embodiment of a substance detection system according to the present invention is shown and referenced generally by numeral 10. By way of example, the present invention will be described as it relates to the detection, measurement and/or characterization of substances in the gaseous state. However, the present invention can be used to detect, measure and/or characterize any substance, i.e., gas, liquid or solid, that exhibits spectrally varying absorption characteristics.

System 10 includes an optics system 12, e.g., a telescope or other lens/mirror system, that collects light from a radiation source 11 such as the earth and atmosphere when system 10 is mounted on a satellite or aircraft, a blackbody when system 10 is used as a laboratory or in-situ instrument, the sun, a laser etc. Radiation from source 11 generally comprises both vertically polarized components V and horizontally polarized components H. The radiation passes between source 11 and system 10 along a sample path SP. The presence of a substance or substances of interest along path SP may affect the radiation in a way that can be detected, measured and/or characterized by system 10.

An optical path switch provided after optics system 12 includes an optical polarizer 14, an optical waveplate 16, a polarization modulator 18 and a polarization beamsplitter 20. Such an optical path switch is disclosed in detail in the afore-mentioned U.S. Pat. No. 5,128,797 to Sachse et al., and will therefore only be described briefly herein.

Optical polarizer 14 is provided after the optics system 12 and is aligned to polarize the incoming radiation in the desired fashion, e.g., vertically in the embodiment depicted in FIG. 1. Polarization modulator 18 (e.g., a photo-elastic modulator) then receives the incident vertically polarized beam and rapidly modulates the output beam between vertical and horizontal polarization. Depending on the measurement application and the type of polarization modulator utilized, the polarization modulation frequency may range from near DC to radio frequencies (RF). The polarization modulator may be used in conjunction with optical waveplate 16. The output of modulator 18 is a time series of alternating vertically polarized components V and horizontally polarized components H as illustrated in FIG. 1. The switching frequency between V and H is determined by the modulation frequency of modulator 18.

Polarization beamsplitter 20 non-mechanically switches the polarization modulated output beam between two paths by, for example, transmitting the beam along path 101 when it is vertically polarized and reflecting it along path 102 when it is horizontally polarized. Alternatively, beamsplitter 20 may be oriented so as to reflect vertically polarized light and to transmit horizontally polarized light. Thus, beamsplitter 20 rapidly diverts the radiation beam alternately between optical paths 101 and 102 depending on the rapidly time-varying state of polarization which is controlled by modulator 18. Note that although paths 101 and 102 are illustrated as being perpendicular to one another, this need not be the case as will be apparent in other embodiments of the present invention described later below.

The radiation beam transmitted along optical path 101 is incident on a gasless optical bandpass filter 22 configured to transmit only a wavelength band of radiation centered at $\lambda_A$ while reflecting other wavelengths. The radiation beam transmitted along optical path 102 is incident on a second gasless optical bandpass filter 24 configured to transmit only a wavelength band of radiation centered at $\lambda_B$ while reflecting other wavelengths. Filters 22 and 24 are selected/constructed such that the bands centered at $\lambda_A$ and $\lambda_B$ are unique as illustrated in FIG. 2. Further, the spectral absorption of the substance to be detected, measured and/or characterized must be different at the two bands. The greater the difference in spectral absorption characteristics between the two bands, the greater the measurement sensitivity of system 10. Accordingly, in an example of the ideal case, spectral absorption occurs only in the band centered at $\lambda_A$ (i.e., spectral absorption in the band centered at $\lambda_B$ would be zero). However, it is to be understood that the present invention will work as long as there is some difference in spectral absorption (of the substance of interest) between the two bands.

The resulting filtered radiation beams passed along optical paths 101 and 102 are directed/reflected by mirrors 26 and 28, respectively, to a polarization beam combiner 30 (e.g., a polarization beamsplitter). Beam combiner 30 outputs a single beam along path 103 in which the beam's polarization state varies in time at the fundamental frequency (and harmonics thereof) of modulator 18. In other words, the output of beam combiner 30 is essentially a time series that alternates between the vertically polarized components V passed by filter 22 and the horizontally polarized components passed by filter 24. The combined radiation beam passes along optical path 103 and is focused by focusing optics 32 onto a detector 34 which is sensitive to the magnitude of the radiation. Because this radiation is in the form of an alternating time series, detector 34 is essentially viewing an amplitude modulated signal. This is because a gas (or other substance) present along sample path SP absorbs radiation from radiation source 11 differentially at the bands centered at $\lambda_A$ and $\lambda_B$. Thus, the differential absorption experienced by the radiation traversing sample path SP is viewed by detector 34 as an amplitude modulated signal. The magnitude of the amplitude modulated signal at the polarization modulation frequency (or its harmonics) is related to the amount or concentration of the substance of interest in sample path SP. Note that if system 10 is subject to changes in the incident radiation due to variations in strength of radiation source 11, turbulence noise, scattering along the optical paths, etc., it may be desirable to normalize the amplitude modulated signal sensed by detector 34. If this is the case, the amplitude modulated signal can be divided by the DC component sensed by detector 34 as is well known in the art.

By way of illustrative example, the present invention will be described briefly for its use in the measurement of hydrocarbons. In this case, filter 22 is chosen so that the band centered at $\lambda_A$ coincides with the carbon-hydrogen bond absorption typical of hydrocarbons (i.e., $\lambda_A$ is approximately 3.4 microns). Filter 24 is chosen so that the band centered at $\lambda_B$ coincides with a wavelength band that is relatively free from hydrocarbon absorption (i.e., $\lambda_B$ is approximately 3.0 microns). By monitoring the magnitude of the amplitude modulated signal sensed by detector 34, the absorption by hydrocarbons present in sample path SP can be detected and measured in a simple fashion, i.e., multiple GFCR devices with multiple gas filter correlation cells (e.g., one for each hydrocarbon of interest) are not required.

Figure 4:
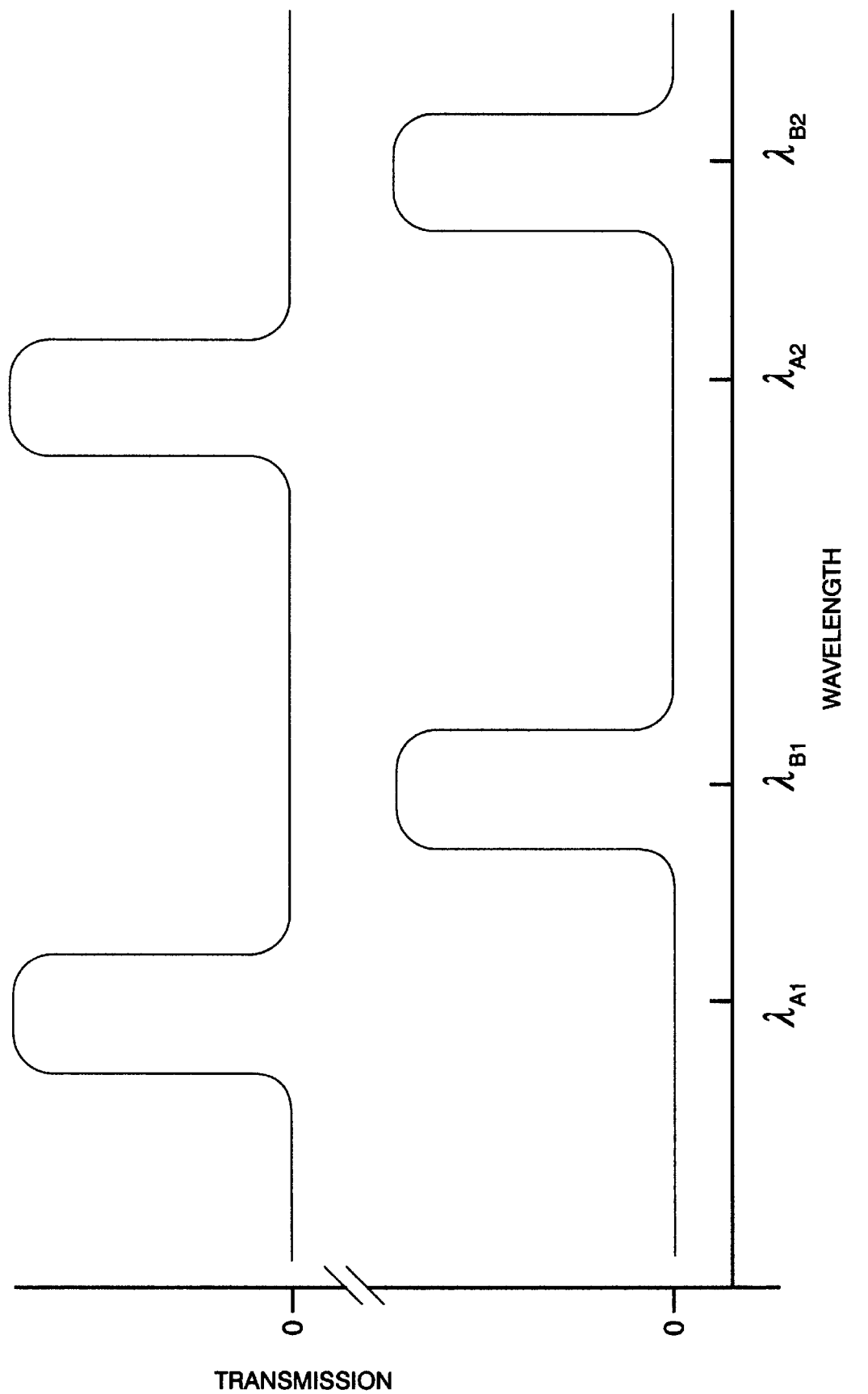
FIG. 4 is a graphical illustration of the filter characteristics of the bandpass filters used in the FIG. 3 embodiment.

Although described relative to the embodiment in FIG. 1, the present invention is not so limited. For example, another embodiment of a substance detection system in accordance with the teachings of the present invention is shown and referenced generally by numeral 200 in FIG. 3. Like reference numerals will be used for those elements that are the same as those used in the FIG. 1 embodiment. The embodiment in FIG. 3 is similar to that in FIG. 1 except that filters 22 and 24 are replaced with dual bandpass filters 220 and 224, respectively. Specifically, filter 220 passes unique wavelength bands centered at $\lambda_{A1}$ and $\lambda_{A2}$ to mirror 26 with other wavelengths being reflected. Filter 224 passes unique wavelength bands centered at $\lambda_{B1}$ and $\lambda_{B2}$ to mirror 28 with other wavelengths being reflected. The bandpass characteristics of filters 220 and 224 are illustrated in FIG. 4. As in the previous embodiment, filter 220 can be configured so that the bands centered at $\lambda_{A1}$ and $\lambda_{A2}$ coincide with radiation bands at which first and second substances of interest are respectively absorbed. Filter 224 can then be configured so that bands centered at $\lambda_{B1}$ and $\lambda_{B2}$ coincide with radiation bands at which the first and second substances are relatively free from absorption.

After the radiation beams are combined at beam combiner 30, the combined beam is directed along optical path 103 to a partitioning or edge filter 226 configured, for example, to reflect wavelength bands centered at $\lambda_{A1}$ and $\lambda_{B1}$ through focusing optics 232 to detector 234 and transmit wavelength bands centered at $\lambda_{A2}$ and $\lambda_{B2}$ through focusing optics 233 to detector 235. Thus, detector 234 is sensitive to the amplitude modulation caused by the differential absorption between the bands centered at $\lambda_{A1}$ and $\lambda_{B1}$ (i.e., associated with the first substance) while detector 235 is sensitive to the amplitude modulation caused by the differential absorption between the bands centered at $\lambda_{A2}$ and $\lambda_{B2}$ (i.e., associated with the second substance). Note that the FIG. 3 embodiment can be expanded to measure three or more substances simultaneously by using the appropriate bandpass (e.g., triple bandpass filter) and beam partitioning filters.

Further, as would be understood by one skilled in the art, other filter configurations are possible. For example, the band centered at $\lambda_{A1}$ could coincide with a radiation band at which the first substance is absorbed; the band centered at $\lambda_{B1}$ could coincide with a radiation band at which the first substance is not absorbed; the band centered at $\lambda_{A2}$ could coincide with a radiation band at which the second substance is not absorbed, and the band centered at $\lambda_{B2}$ could coincide with a radiation band at which the second substance is absorbed.

Figure 5:
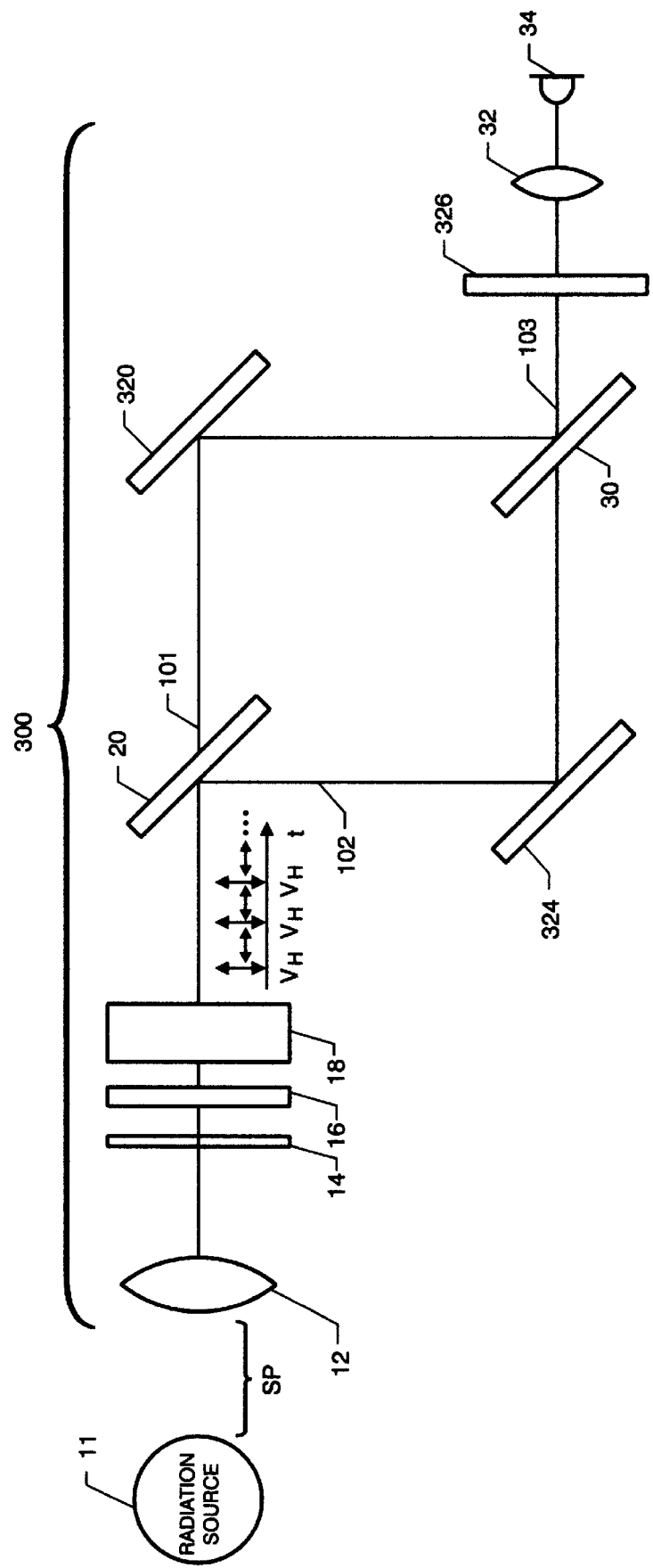
FIG. 5 is a schematic representation of another embodiment of the present invention in which bandpass filters are used in reflection.
Figure 6:
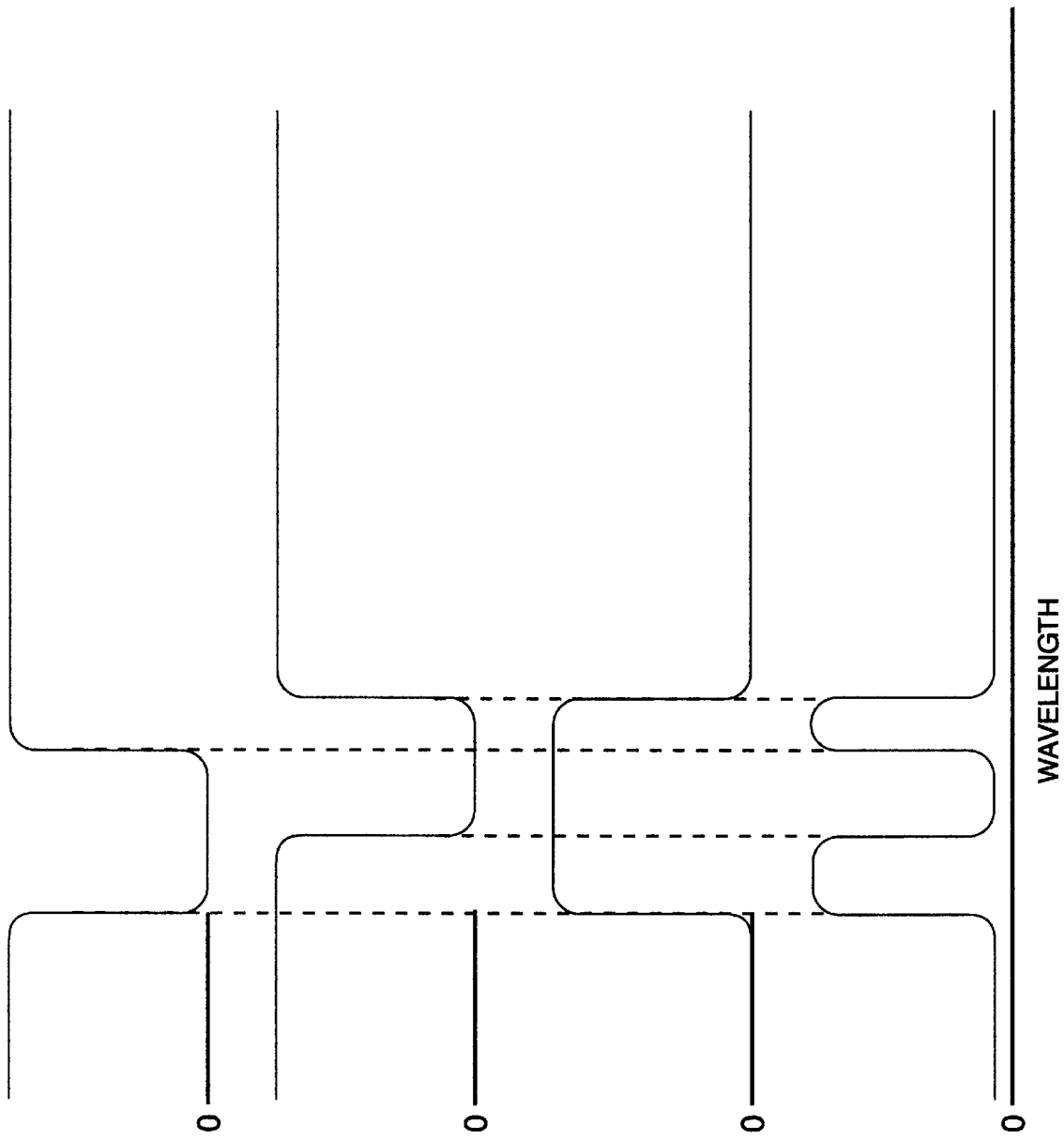
FIG. 6A is a graphical illustration of one filter's characteristics used in the FIG. 5 embodiment.
FIG. 6B is a graphical illustration of the other filter's characteristics used in the FIG. 5 embodiment.
FIG. 6C is a graphical illustration of a bracketing bandpass filter's characteristics used in the FIG. 5 embodiment.
FIG. 6D is a graphical illustration of the spectral information reaching the detector in the FIG. 5 embodiment.

Still another embodiment of the present invention is illustrated in FIG. 5 and referenced generally by numeral 300. Once again, like reference numerals will be used for those elements that are the same as those used in the FIG. 1 embodiment. In FIG. 5, bandpass filters 320 and 324 are used in reflection instead of transmission. That is, as illustrated respectively in FIGS. 6A and 6B, filter 320 reflects all wavelengths (to beam combiner 30) except for the wavelength band centered at $\lambda_A$ and filter 324 reflects all wavelengths (to beam combiner 30) except the wavelength band centered at $\lambda_B$. As in the FIG. 1 embodiment, absorption at the bands centered at $\lambda_A$ and $\lambda_B$ is different for the substance of interest. The beams are combined by beam combiner 30 and transmitted along optical path 103 to a bracketing bandpass filter 326 having a band pass characteristic that spans the two wavelength bands isolated by filters 320 and 324. The transmission characteristics of bracketing bandpass filter 326 are illustrated in FIG. 6C. Note that bracketing filter 326 could be replaced with a dual bandpass filter. Either way, focusing optics 32 and detector 34 receive a signal magnitude affected by absorption in the two bands illustrated in FIG. 6D. Since each band is alternately received by detector 34, an amplitude modulated signal is monitored. The advantages of the FIG. 5 embodiment include fewer components and the preservation of the majority of the radiation for further processing as will now be described with the aid of FIG. 7. The present invention could also be practiced by using dual (or triple) bandpass filters (in place of filters 320 and 324) and wavelength partitioning, optics/detectors to enable the measurement of several substances simultaneously.

Figure 7:
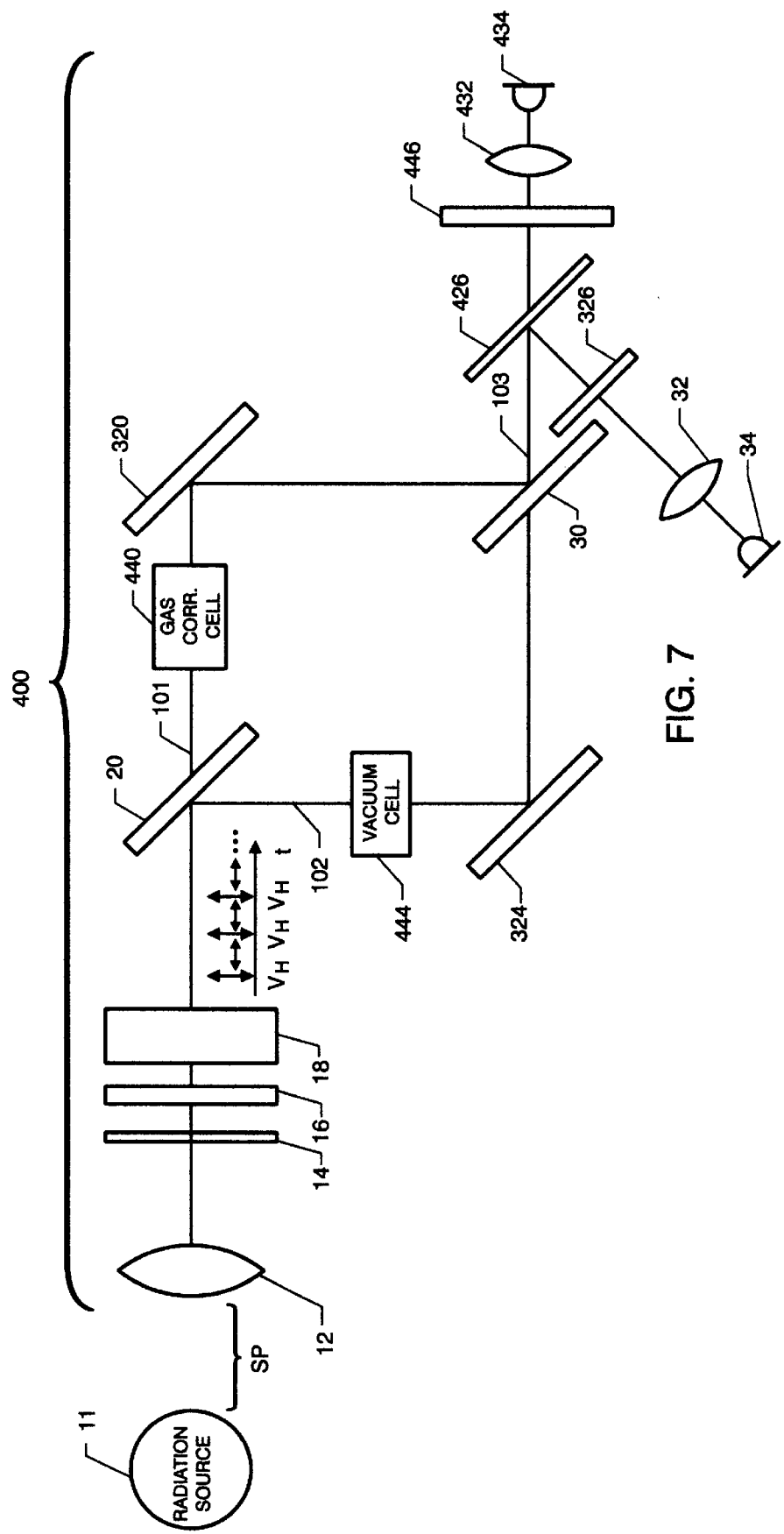
FIG. 7 is a schematic representation of another embodiment of the present invention in which differential absorption measurements and gas filter correlation radiometry (GFCR) measurements are made simultaneously.

The embodiment illustrated in FIG. 7, and referenced generally by numeral 400, is used to make differential absorption and gas filter correlation measurements simultaneously. As before, like reference numerals are used for elements that are common with the FIG. 5 embodiment. System 400 is useful in measurement applications that require both high measurement specificity for certain gas species and measurement of a broad class of gases. An example is the remote measurement of car exhaust. In this measurement, high gas specificity is needed to accurately measure NO because of the overlap of a strong water vapor band at 5.2 microns. At the same time, a "total hydrocarbon" measurement is desired in the 3.4 micron carbon-hydrogen absorption region. In other words, the measurement of a specific hydrocarbon is not desired. Rather, the measurement of the net differential absorption in this C—H stretch region is desired as some indication of "total hydrocarbons". Such conflicting types of simultaneous measurements are possible in the present invention. That is, the present invention makes it possible to use the GFCR technique for the NO measurement and the differential absorption technique for the "total hydrocarbon" measurement.

In FIG. 7, a gas correlation cell 440 is disposed in optical path 101 and a vacuum cell 444 is disposed in optical path 102. Cells 440 and 444 enable a GFCR measurement while filters 320 and 324 enable the differential absorption measurement as described above with reference to FIG. 5. More specifically, the radiation beams are combined at beam combiner 30. The combined beam is partitioned at edge filter 426 which, for example, transmits the wavelength region associated with the GFCR measurement to a GFCR bandpass filter 446, focusing optics 432 and detector 434 so that a standard GFCR measurement can be made as is well known in the art. Edge filter 426 reflects other wavelengths to bracketing or bandpass filter 326 which functions as in the previous embodiment of FIG. 5.

Figure 8:
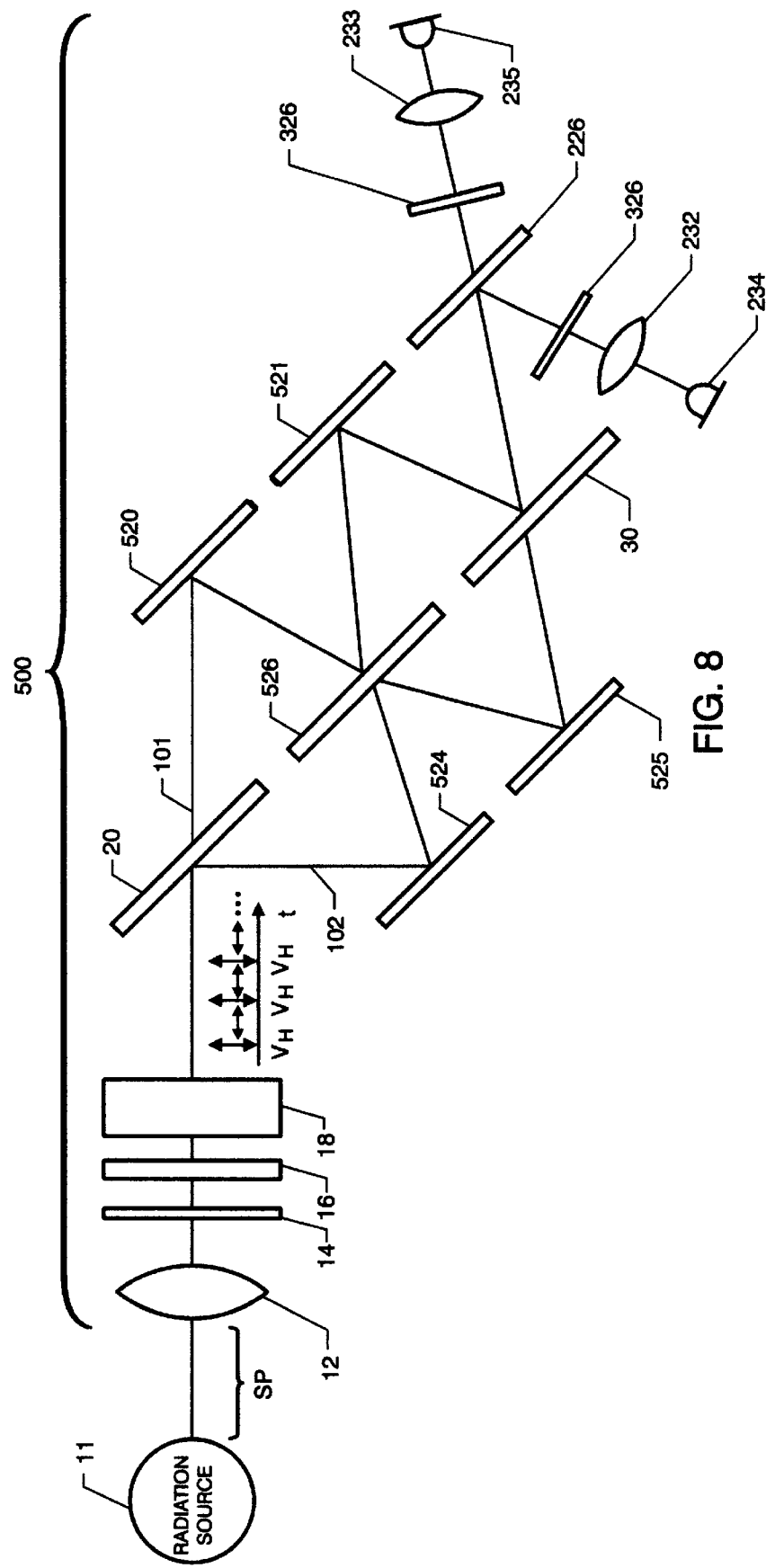
FIG. 8 is a schematic representation of another embodiment in which two substances can be detected/measured simultaneously using bandpass filters in reflection.

Another way to detect or measure two substances simultaneously using bandpass filters in reflection is shown and referenced generally by numeral 500 in FIG. 8. That is, system 500 is an alternative construction that achieves the results described above with respect to FIG. 3. In optical path 101, a first bandpass filter 520 reflects all wavelengths except those in a first band centered at $\lambda_{A1}$ towards one side of a two-sided mirror 526. Mirror 526 reflects the radiation to a second bandpass filter 521 that reflects all wavelengths except those in a second band centered at $\lambda_{A2}$. In a similar fashion, bandpass filters 524/525 and mirror 526 cooperate to remove wavelength bands centered at $\lambda_{B1}$ and $\lambda_{B2}$ in optical path 102. The single beam output from beam combiner 30 can then be processed as described in the FIG. 3 embodiment. Detection optics may include bracketing filters 326 as needed.

Figure 9:
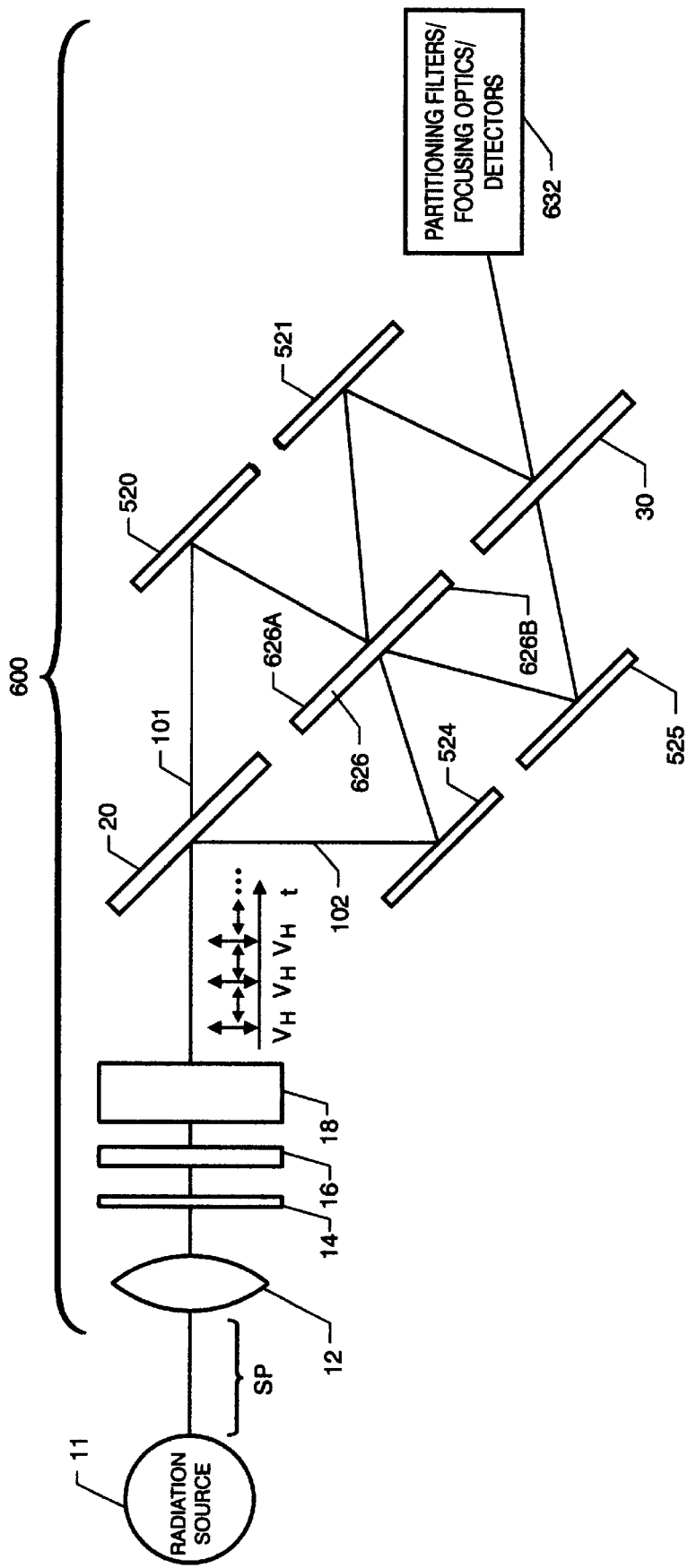
FIG. 9 is a schematic representation of another embodiment in which three substances can be detected/measured simultaneously.

Still another embodiment of the present invention is shown in FIG. 9 and is referenced generally by numeral 600. System 600 is similar to system 500 except that mirror 526 is replaced with a two-sided bandpass absorber 626. Absorber 626 is configured on side 626A to absorb radiation in a third wavelength band centered on $\lambda_{A3}$ while reflecting all other wavelengths. This can be accomplished by designing a bandpass filter stack that transmits the band centered at $\lambda_{A3}$ which is then absorbed internally. For example, the substrate material could strongly absorb this wavelength band. On the other side 626B of absorber 626 is a second filter stack that selectively transmits/absorbs a wavelength band centered at $\lambda_{B3}$. After being combined at beam combiner 30, a system of partitioning filters/focusing optics/detectors 632, similar to the systems disclosed in the embodiments of FIGS. 3, 7 and 8, are used to partition the single beam so that the differential absorption between each wavelength band pair (i.e., wavelength band pairs centered at $\lambda_{A1}$ and $\lambda_{B1}$, $\lambda_{A2}$ and $\lambda_{B2}$, and $\lambda_{A3}$ and $\lambda_{B3}$) can be individually and simultaneously sensed.

Figure 10:
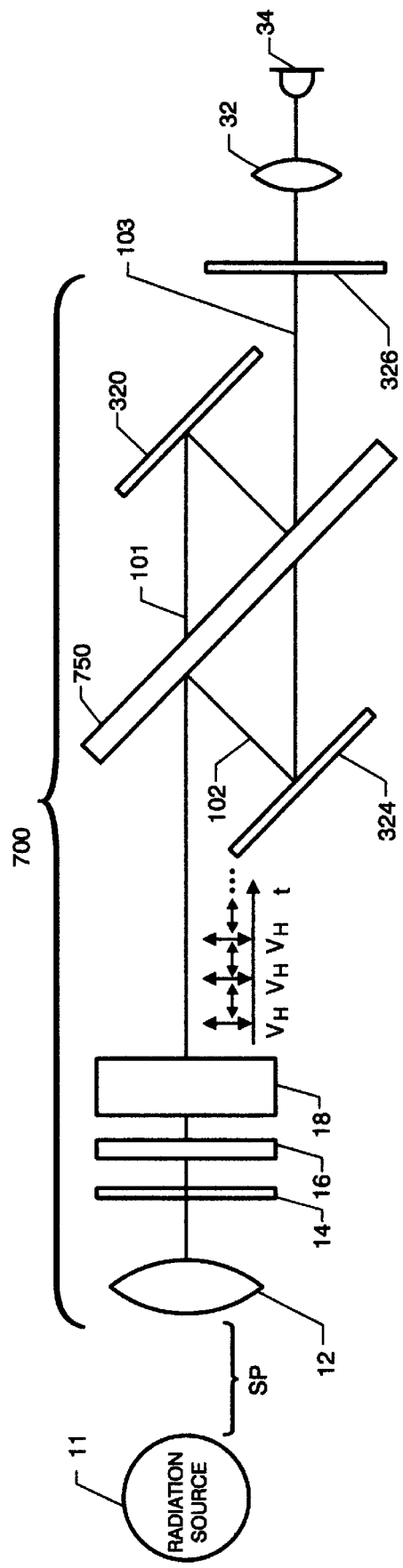
FIG. 10 is a schematic representation of another embodiment of the present invention.

In still another embodiment of the present invention, system 700 illustrated in FIG. 10 is an alternative construction for the FIG. 5 embodiment. System 700 is a compact configuration of the present invention in which optical path 101 exits a combination beamsplitter/combiner 750 at an acute angle thereto. A single optical element can be used for beamsplitting and beam combining by, for example, configuring the device's wire grids (not shown) to transmit horizontal polarization in the beamsplitter portion and to transmit vertical polarization in the beam combiner portion.

The advantages of the present invention are numerous. Substance detection and measurement can be achieved without using gas cells. However, the present invention can be configured to provide for simultaneous differential absorption and GFCR measurements. Further, multiple differential absorption measurements associated with multiple substances can be made simultaneously.

Although the invention has been described relative to a specific embodiment thereof, there are numerous variations and modifications that will be readily apparent to those skilled in the art in light of the above teachings. It is therefore to be understood that, within the scope of the appended claims, the invention may be practiced other than as specifically described.

What is claimed as new and desired to be secured by Letters Patent of the United States is:

1. A system for detecting a substance comprising:

an optical path switch for receiving radiation passing along a sample path of interest, said optical path switch dividing said radiation into a time series of alternating first polarized components and second polarized components orthogonal to said first polarized components, said optical path switch transmitting said first polarized components along a first optical path and said second polarized components along a second optical path;

a first gasless optical filter train disposed in said first optical path for filtering said first polarized components to isolate at least a first wavelength band wherein first filtered radiation is generated;

a second gasless optical filter train disposed in said second optical path for filtering said second polarized components to isolate at least a second wavelength band wherein second filtered radiation is generated, wherein said first wavelength band and said second wavelength band are unique and wherein spectral absorption of a substance of interest is different at said first wavelength band as compared to said second wavelength band;

a beam combiner disposed to receive said first filtered radiation and said second filtered radiation for combining said first filtered radiation and said second filtered radiation to form a combined beam of radiation; and detector means disposed to monitor magnitude of at least a portion of said combined beam alternately at said first wavelength band and said second wavelength band as an indication of the concentration of said substance in said sample path.

2. A system as in claim 1 wherein said first gasless optical filter includes a first optical filtering means for passing only said first wavelength band to form said first filtered radiation, and wherein said second gasless optical filter includes a second optical filtering means for passing only said second wavelength band to form said second filtered radiation.

3. A system as in claim 1 wherein said first gasless optical filter includes a first optical filtering means for passing all wavelengths except said first wavelength band to form said first filtered radiation, and wherein said second gasless optical filter includes a second optical filter means for passing all wavelengths except said second wavelength band to form said second filtered radiation.

4. A system as in claim 3 further comprising a gas filter correlation radiometer coupled to said optical path switch, said gas filter correlation radiometer using one of said first polarized components and said first filtered radiation and using one of said second polarized components and said second filtered radiation to measure the concentration of at least one gas species in said sample path.

5. A system as in claim 1 wherein said first gasless optical filter includes first optical filtering means for isolating a plurality of unique first wavelength bands, and wherein said second gasless optical filter includes second optical filtering means for isolating a plurality of unique second wavelength bands said system further comprising:

- a beam partitioner disposed to receive said combined beam and for partitioning said combined beam into a plurality of partitioned beams, each of said plurality of partitioned beams including one of said plurality of unique first wavelength bands and one of said plurality of unique second wavelength bands, wherein spectral absorption of a substance of interest is different at one of said one of said plurality of unique first wavelength bands as compared to said one of said plurality of unique second wavelength bands, wherein said detector means comprises a plurality of detectors, each of said plurality of detectors disposed to receive one of said plurality of partitioned beams.

6. A system as in claim 1 wherein said first polarized components are vertically polarized and said second polarized components are horizontally polarized.

7. A system as in claim 1 wherein said detector means is harmonically synchronized to a frequency at which said time series alternates between said first polarized components and said second polarized components.

8. A substance detection system comprising:

- an optical path switch for receiving radiation passing along a sample path of interest, said optical path switch dividing said radiation into a time series of alternating first polarized components and second polarized components orthogonal to said first polarized components, said optical path switch transmitting said first polarized components along a first optical path and said second polarized components along a second optical path;
- a first gasless optical filter train disposed in said first optical path for filtering said first polarized components to pass all wavelengths except those in a first wavelength band wherein first filtered radiation is generated;
- at least one gas correlation cell disposed in said first optical path for filtering one of said first polarized components and said first filtered radiation at spectral regions different from that of said first wavelength band;
- a second gasless optical filter train disposed in said second optical path for filtering said second polarized components to pass all wavelengths except those in a second wavelength band wherein second filtered radiation is generated, wherein said first wavelength band and said second wavelength band are unique and wherein spectral absorption of a substance of interest is different at said first wavelength band as compared to said second wavelength band;
- a vacuum cell disposed in said second optical path;
- a beam combiner disposed to receive said first filtered radiation and said second filtered radiation for combining said first filtered radiation and said second filtered radiation to form a combined beam of radiation;
- first detecting means disposed to monitor magnitude of at least a portion of said combined beam alternately at said first wavelength band and said second wavelength band as an indication of the concentration of said substance in said sample path; and
- second detecting means disposed to sense a difference in intensity between said first filtered radiation and said second filtered radiation at said spectral regions to measure the concentration of at least one gas species in said sample path.

9. A system as in claim 8 wherein said first polarized components are vertically polarized and said second polarized components are horizontally polarized.

10. A system as in claim 8 wherein said first detecting means is harmonically synchronized to a frequency at which said time series alternates between said first polarized components and said second polarized components.

* * * * *